United States Patent [19]
Holloway

[11] Patent Number: 5,415,747
[45] Date of Patent: May 16, 1995

[54] CAPILLARY ELECTROPHORESIS USING ZWITTERION-COATED CAPILLARY TUBES

[75] Inventor: Robert R. Holloway, Montara, Calif.

[73] Assignee: Hewlett-Packard Company, Palo Alto, Calif.

[21] Appl. No.: 107,393

[22] Filed: Aug. 16, 1993

[51] Int. Cl.$^6$ .................... G01N 27/26; G01N 27/447
[52] U.S. Cl. .............................. 204/180.1; 204/299 R
[58] Field of Search ......................... 204/180.1, 299 R

[56] References Cited

U.S. PATENT DOCUMENTS

| | | | |
|---|---|---|---|
| 5,006,313 | 4/1991 | Swedberg | 204/299 R X |
| 5,015,350 | 5/1991 | Wiktorowicz | 204/180.1 |
| 5,143,753 | 9/1992 | Novotny et al. | 204/299 R X |
| 5,151,164 | 9/1992 | Blanchard et al. | 204/182.1 |
| 5,180,475 | 1/1993 | Young et al. | 204/180.1 |
| 5,181,999 | 1/1993 | Wiktorowicz | 204/180.1 |

FOREIGN PATENT DOCUMENTS

| | | |
|---|---|---|
| 494686 | 7/1992 | European Pat. Off. . |
| 519203 | 12/1992 | European Pat. Off. . |

OTHER PUBLICATIONS

Mark A. Strege and Avinash L. Lagu, "Studies of Migration Time Reproducibility of Capillary Electrophoretic Protein Separations" Journal of Liquid Chromatography, 16(1) (1993) 51-68 no month available.

Hilmer Sorensen et al. "High-performance capillary electrophoresis for the determination of trypsin and chymotsypsin inhibitors and their assoication with trypsin, chymotrypsin and monoclonal antibodies" Journal of Chromatography A, vol. 652 No. 1 (Oct. 15, 1993) 189-198.

H. K. Kristensen and S. H. Hansen "Separation of polymyxins by micellar electrokinetic capillary chromatography" Journal of Chromatography 628(1993) 309-315 No month available.

Rick J. Krueger et al "Analysis of endoproteinase Arg Caction or adrenocorticotrophic hormone by capillary electrophoresis and reversed-phase high-performance liquid chromatography" Journal of Chromatography, vol. 543, No. 2 (May 10, 1991).

H. K. Kristensin and S. H. Hansen, "Micellar Electrokinetic Chromatographic Separation of Basic Polypeptides with Equal Mass to Charge Ratio Using Dynamically Modified Silica Capillaries" Journal of Liquid Chromatography 16(14) (1993) 2961-2975 No month available.

U. R. Tjaden et al "Automated isotachophoretic analyte focusing for capillary zone electrophoresis in a single capillary using hydrodynamic back-pressure programming" Journal of Chromatography, vol. 641, No. 1 (Jul. 2, 1993) 155-162.

Ranjit R. Deshmukh & Milan Bier, "Counterflow in isotachophoresis: Computer simulation and experimental studies" Electrophoresis, vol. 14, No. 3 (Mar. 1993) 205-213.

F. A. Chen et al., "Use of High Ionic Strength Buffers for the Separation of Proteins and Peptides with Capillary Electrophoresis", J. Liq. Chromatog. 15(6 & 7):1143-1161 (1992) No month available.

K. A. Cobb et al., "Electrophoretic Separations of Proteins in Capillaries with Hydrolytically Stable Surface Structures," Anal. Chem. 62:2478-2483 (Nov. 1990).

(List continued on next page.)

Primary Examiner—John Niebling
Assistant Examiner—John S. Starsiak, Jr.

[57] ABSTRACT

A method and apparatus for controlling the velocity of electroosmotic flow (EOF) in high performance capillary electrophoresis (HPCE) are provided. The interior surface of the capillary tube is coated with a zwitterionic coating, such that the pH range within which EOF velocity may be controlled is broadened. The zwitterionic coating involves covalent, ionic or adsorptive binding of a zwitterionic species such as phosphoryl choline to the capillary wall.

14 Claims, 2 Drawing Sheets

OTHER PUBLICATIONS

Kohr et al., "Capillary Electrophoresis with Surface Coated Capillaries", *J. Microcol. Sep.* 3:491–495 (1991) No month available.

Maa et al., "Impact of Wall Modifications on Protein Elution in High Performance Capillary Electrophoresis", in *J. High Res. Chromatogr.* 14:65–67 (Jan. 1991).

Schomburg, "Polymer Coating of Surfaces in Column Liquid Chromatography and Capillary Electrophoresis", *Trends Anal. Chem.* 10:163–169 (1991).

Swedberg, "Characterization of Protein Behavior in High-Performance Capillary Electrophoresis Using a Novel Capillary System", *Analytical Biochem.* 185:51–56 (1990) No month available.

Swedberg, "Use of Non–Ionic and Zwitterionic Surfactants to Enhance Selectivity in High Performance Capillary Electrophoresis. An Apparent Micellar Electrokinetic Capillary Chromatography Mechanism", *J. Chromatogr.* 503:449–452 (1990) No month available.

CAPILLARY ELECTROPHORESIS USING ZWITTERION-COATED CAPILLARY TUBES

BACKGROUND OF THE INVENTION

1. Technical Field

The present invention relates generally to capillary electrophoresis. More specifically, the invention relates to a novel method for carrying out capillary electrophoresis using zwitterion-coated capillary tubes. The use of zwitterionic coatings in turn provides for greater control over electroosmotic flow and minimizes adsorption of components contained within the sample solution. The invention additionally relates to an apparatus for performing the novel method.

2. Description of the Related Art

Separation of chemical entities is possible using the technique of "electrophoresis", a method which is premised upon the differential migration of solutes in an electric field. In high performance capillary electrophoresis (HPCE), a technique developed in the early 1980's, electrophoretic separation is performed in narrow capillary tubes, typically 25 µm to 75 µm in diameter, which are filled with a conducting solution, normally a buffer. A small amount of sample is introduced at one end of the capillary tube, followed by application of a high potential difference across the ends of the tube. Electroosmotic flow (also termed "electroendoosmotic flow", or EOF) and differences in electrophoretic mobilities combine to provide a spatial separation of the constituents of the sample solution.

HPCE has numerous advantages, particularly with respect to the detrimental effects of Joule heating. The high electrical resistance of the narrow capillary tube enables the application of very strong electric fields, in the range of 100 to 500 V/cm, with only minimal heat generation. Additionally, the large surface-to-volume ratio of the capillary enables efficient dissipation of the heat that is generated during the separation process. Further, the use of high electric fields gives rise to shorter analysis times (on the order of ten minutes or less) than required for conventional electrophoretic separations, high separation efficiency, and superior resolution. Peak efficiency, often in excess of $10^5$ theoretical plates, is due in part to the plug profile of the EOF, which also enables the simultaneous analysis of all solutes, regardless of charge. Finally, HPCE allows for use of relatively simple instrumentation, on-line detection through the capillary wall, and very small sample volumes (on the order of 1 to 10 nl).

The underlying principles of electrophoretic separation are quite simple, and may be summarized as follows. Separation of constituents in a sample is enabled based on differences in solute velocity in an electric field. The velocity of an ion is given by the relationship:

$$v = \mu_e E$$

where v is the ion velocity, $\mu_e$ is the electrophoretic mobility, and E is the applied electric field. The electrophoretic mobility, for a given ion and medium, is a constant which is characteristic of that ion, and may be represented as:

$$\mu_e = q \div 6\pi^n r$$

where q is the ion charge, $n$ is the solution viscosity, and r is the ion radius. From this relationship, it is evident that small, highly charged species have high mobilities whereas large, minimally charged species have low mobilities. It will be appreciated that the electrophoretic mobility found in standard tables is a physical constant, determined at the ideal conditions of full solute charge and infinite dilution, and differs somewhat from the electrophoretic mobility that is determined experimentally. The experimental value is termed the "effective mobility" and is highly dependent on the pH of the sample in the bulk fluid.

The pH of the sample undergoing analysis is important in another respect as well. The EOF velocity $V_{EOF}$, may be defined as follows:

$$v_{EOF} = (\epsilon \zeta / n) E$$

where $\epsilon$ is the dielectric constant of the sample fluid and $\zeta$ is the zeta potential (and $\epsilon \zeta / n$ is the electroosmotic mobility, $\mu_{EOF}$). The zeta potential $\zeta$ is essentially determined by the surface charge on the capillary wall, which is in turn related to the presence of the surface silanol groups on the interior of the capillary tube. These surface silanol groups are predominantly deprotonated at higher pH (such that they are in the form of anionic, Si—O$^-$ groups) and protonated at lower pH (such that they are in the form of ionically neutral Si—OH groups). The magnitude of the EOF velocity, then, is strongly pH dependent.

In some cases, a higher EOF velocity is preferred, i.e., when working with materials that are readily separated. In many other cases, however, a high $V_{EOF}$ can result in elution of solute before separation has occurred, and a lower EOF velocity is preferred. In still other cases, an EOF flow counter to the direction of ion migration is desirable. Accordingly, the ability to control EOF velocity is highly desirable. To date, however, electronic control of EOF velocity has been possible only for electrophoretic separations conducted at a very low pH.

The present invention is addressed to the aforementioned need in the art, as it is directed to a method for broadening the pH range within which EOF can be regulated, i.e., within which EOF velocity can be controlled. The invention is premised on the discovery that the "electric double layer" caused by the buildup of negative charges on the interior of the capillary tube may be controlled by coating the interior of the capillary with a zwitterionic species. In addition to broadening the pH range within which EOF velocity may be controlled, the zwitterionic coatings minimize adsorption of sample constituents to the capillary wall via ionic attraction to the ionized silanol groups, and thus enhance the efficiency and resolution of separation.

SUMMARY OF THE INVENTION

Accordingly, the invention is directed to a capillary electrophoresis method and apparatus for separating component elements contained within a sample solution such that EOF control is enabled within a broader pH range than previously possible. The invention is additionally directed to a fused silica capillary tube coated on its interior surface. The coated capillary tube is provided within the context of an electrophoresis apparatus having a means for introducing the sample solution into the capillary tube, a means for applying an electric field across the length of the capillary tube, and a component detecting means. The interior of the capillary is coated with a zwitterionic species.

Typically, the zwitterionic coating is a zwitterionic species bound to the interior surface of the capillary tube via a covalent linkage, Alternatively, the coating may be a zwitterionic species which is adsorbed on or ionically bound to the interior surface of the capillary tube. A particularly preferred zwitterionic coating is phosphoryl choline, covalently bound to the silanol groups on the capillary wall through a siloxane linkage.

As alluded to above, the use of a zwitterionic coating on the interior of the capillary tube provides for several important advantages which are not provided by previously known capillary electrophoresis techniques.

DETAILED DESCRIPTION OF THE INVENTION

Figure 1:
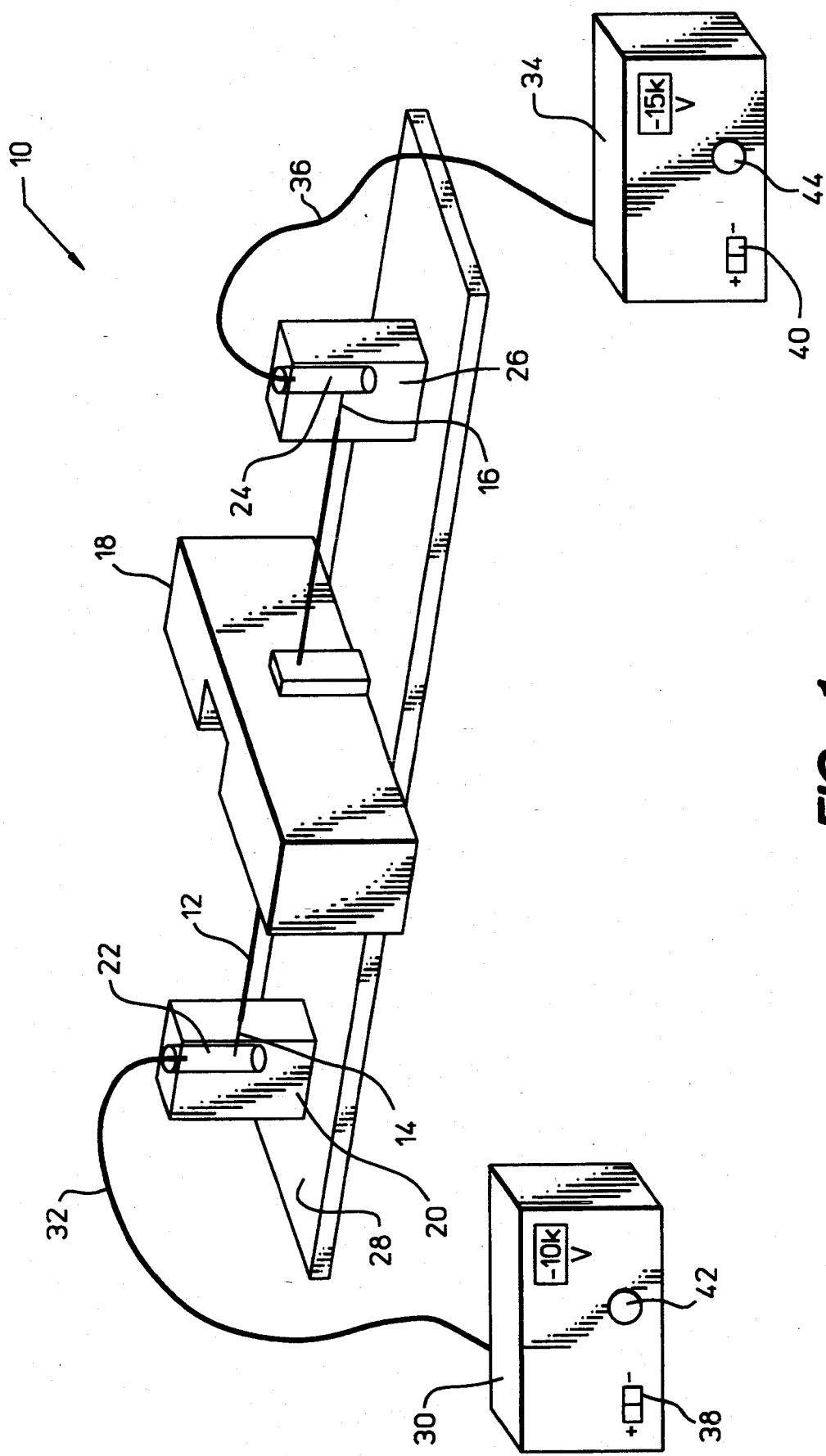
FIG. 1 is a schematic view of a capillary electrophoresis apparatus which may be used in connection with the invention.

Before the invention is described in detail, it is to be understood that this invention is not limited to specific zwitterionic coatings or to specific modes for incorporating zwitterionic coatings into a capillary electrophoresis system as such may vary. It is also to be understood that the terminology used herein is for the purpose of describing particular embodiments only and is not intended to be limiting.

In this specification and in the claims which follow, reference will be made to a number of terms which shall be defined to have the following meanings:

The term "zwitterionic species" is used in its conventional sense to mean a single molecular entity containing both a cationic group and an anionic group at a particular pH range.

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. Preferred alkyl groups herein contain 1 to 12 carbon atoms. The term "lower alkyl" intends an alkyl group of one to six carbon atoms, e.g., methyl, ethyl, n-propyl, isopropyl, n-butyl, isobutyl, t-butyl, and the like.

The term "alkylene" as used herein refers to a difunctional saturated branched or unbranched hydrocarbon chain containing from 1 to 24 carbon atoms, and includes, for example, methylene (—$CH_2$—), ethylene (—$CH_2$—$CH_2$—), propylene (—$CH_2$—$CH_2$—$CH_2$—), 2-methylpropylene [—$CH_2$—$CH(CH_3)$—$CH_2$—], hexylene [—$(CH_2)_6$—] and the like. The term "lower alkylene" refers to an alkylene group of one to six carbon atoms, e.g., methylene, ethylene, propylene, and the like.

The term "arylene" refers to a difunctional aromatic moiety; "monocyclic arylene" refers to a phenylene group. These groups may be substituted with up to four ring substituents which are generally although not necessarily selected from the group consisting of halogen, alkyl (typically lower alkyl), alkoxy (typically lower alkoxy), acyl (typically lower acyl), and nitro. Other aromatic substituents are possible as well, providing that they are not ionically charged at the pH of the electrophoretic separation.

The term "alkarylene" refers to a difunctional moiety containing an arylene group and an alkylene group. The term "lower alkarylene" refers to an alkarylene group containing less than 12 carbon atoms.

The term "oxyalkylene" refers to an alkylene linkage containing 1 to 24 carbon atoms and 1 to 3 ether linkages. Preferred oxyalkylene groups are alkylene linkages containing a single ether linkage at a terminus, i.e., —$(CH_2)_n$—O—. The term "lower oxyalkylene" intends an oxyalkylene group containing 1 to 6 carbon atoms and a single, preferably terminal, ether linkage.

"Halo" or "halogen" refers to fluoro, chloro, bromo or iodo, and usually relates to halo substitution for a hydrogen atom in an organic compound. Of the halos, chloro and fluoro are generally preferred.

A "siloxane" as used herein is a compound which contains one or more silicon-oxygen bonds. The term "siloxyl" refers to a siloxane radical. The term "silyl" unless otherwise specified, intends a linkage which contains a silicon atom.

In a preferred embodiment of the invention, a zwitterionic coating is incorporated into an electrophoresis apparatus by covalently bonding a zwitterionic species to the interior surface of the capillary tube. The zwitterionic species may be bonded through a siloxane linkage or it may be bonded through a silicon-carbon bond. It may be bonded directly, through one or more linking groups, or through a polymeric species; however, it is preferred that the distance between the zwitterionic species and the capillary tube surface be minimized.

Generally, the zwitterionic species used in conjunction with the method of the invention contains both an $O^-$ moiety and a quaternary ammonium group. The anionic moiety will generally be in the form of a phosphoryl, sulfonate or carboxylate group while the quaternary ammonium group will typically be of the formula —$NR_3^+$ where R is lower alkyl, preferably methyl. The zwitterionic species may accordingly be represented as:

 (1)

 (2)

or

 (3)

where, in formula (1), $L^1$ and $L^2$ are optional linking groups, $X^-$ is an anionic species, and * represents the point of attachment of the zwitterionic species to the silica surface; the same is true for formula (2), although this representation does not contain the linking group $L^2$. $L^1$ and $L^2$ are generally selected from the group consisting of alkylene, oxyalkylene, alkylene containing an ester linkage (i.e., —$(CH_2)_a$—COO—$(CH_2)_b$ where a and b are integers in the range of 0 to 24 inclusive, with the proviso that not both are 0), alkarylene, silyl, siloxyl, and combinations thereof. In a preferred embodiment, $L^1$ is selected from the group consisting of lower alkylene, lower oxyalkylene —O—$(CH_2)_c$— where c is an integer in the range of 1 to 6 inclusive, lower alkylene with a single ester linkage (i.e., —$(CH_2)_a$—COO—$(CH_2)_b$) where a and b are integers in the range of 1 to 6 inclusive, with the proviso that the sum of a and b is 6 or less), siloxyl —O—Si—, and combinations thereof. With regard to the "backbone" anionic species, it is preferred that $X^-$ be phosphoryl, i.e., —O—(PO)O$^-$—.

In formula (3), $L^3$ and $L^4$ are linking groups as defined above with respect to $L^1$ and $L^2$; however, $L^4$ is optional while $L^3$, as may be readily deduced from the structural formula, is not. Preferred $L^3$ and $L^4$ linkages are the same as the preferred $L^1$ and $L^2$ identified above. With regard to the pendant anionic species, it is preferred that $Y^-$ be sulfonate —SO$_3$H$^-$ or carboxylate —CO$_2^-$. Again, * represents the point of attachment of the zwitterionic species to the silica surface.

Structural representations (4), (5) and (6) illustrate covalent attachment of the zwitterionic species of formulae (1), (2) and (3), respectively, to a silicon atom contained within the silica surface:

(4)

(5)

(6)

In these structures and elsewhere herein, Si$^1$ represents a surface silicon atom contained within the capillary wall.

If the zwitterionic species is covalently attached to the capillary tube surface through a siloxane bond, the siloxane linkage will typically be of the formula Si$^1$—O—Si(OR$^1$)$_2$—, where R$^1$ is lower alkyl, such that —O—Si(OR$^1$)$_2$— is a part of L$^1$, as shown in Formulae (4) and (5), or a part of L$^3$, as shown in Formula (6). This type of surface modification may be readily effected by reaction of the surface silanol groups Si$^1$—OH with a monomeric siloxane having the formula R—Si(OR$^1$)$_3$ where R is or contains the zwitterionic species and R$^1$ is as defined above. That is, R will be (or will contain) —X$^-$—L$^2$—NR$_3^+$ or —L$^3$(NR$_3^+$)—L$^4$—Y$^-$. Such reactions are well known in the art and are described, for example, by Halasz and Sebastian, *Angew Chem. (Int. Ed.)* 8:453 (1969), Duel et al., *Helv. Chim. Acta* 119:1160 (1959), and Hunter et al., *Indust. and Engin. Chem.* 39:1389 (1947), as well as in U.S. Pat. No. 3,965,179 to Sebastian.

In a particularly preferred embodiment, the covalently bound zwitterionic species may be represented by the formula

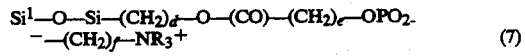
(7)

where, again, Si$^1$ is a silicon atom contained within the interior surface of the capillary tube, d, e and f are integers in the range of 1 to 6 inclusive, and R is lower alkyl. One example of such a species is phosphoryl choline.

Alternatively, the zwitterionic species may be covalently bound to the silica surface through a silicon-carbon linkage. Such linkages are stable to extremes of pH, and may be readily prepared using methods known in the art, such as described in U.S. Pat. No. 4,904,632 to Pesek et al. Briefly, the method involves halogenation of the silica surface using, typically, a Lewis base halogenating reagent such as thionyl chloride, thionyl bromide or phosgene, in an anhydrous, aprotic solvent such as toluene. A vacuum is applied to the capillary, such that the reactants are drawn therein. The reaction is allowed to proceed until completion, typically involving a reaction temperature of approximately 50° C. or higher and a reaction time of about 16-18 hours, at which point it may be presumed that the majority of the surface silanol groups have been converted to Si—Z groups, where Z is a halogen atom. This step is then followed by alkylation using either a Grignard reagent Zw—MgBr or ZwLi where Zw represents the zwitterionic species, i.e., either of those illustrated in Formulae (1) and (2). This produces a covalently bound zwitterionic species wherein the linkage to the silica surface is through a direct Si—C bond. A similar reaction is described by K. A. Cobb et al., in *Anal. Chem.* 62:2478-2483 (1990).

The zwitterionic species may also be covalently bound to the silica surface through Si—N linkages, as will be appreciated by those skilled in the art of organosilicon chemistry. Generally, binding the zwitterionic species in this way will involve halogenation of the silica surface as above, followed by reaction with a silazane compound. The zwitterionic species may be incorporated within the selected silazane compound prior to reaction, or it may be attached thereto subsequently.

Alternatively, the zwitterionic species may be bound to the silica surface through ionic attraction or adsorption. The former method will involve preparation of a salt

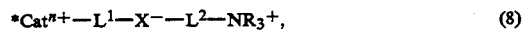
(8)

(9)

or

(10)

where Cat is any suitable cation, e.g., a quaternary ammonium cation such as C$_6$H$_6$—CH$_2$—NR$_2^+$—, and L$^1$, L$^2$, L$^3$, L$^4$, X, Y and R are as defined above with respect to Formulae (1) through (4). This is then allowed to form a salt with the ionized surface silanol groups Si—O$^-$.

Still another technique which could be used to bind the zwitterionic species to the silica surface of the capillary wall is simple adsorption of the selected zwitterion to the interior surface of the capillary tube.

As will be appreciated by those working in the field of capillary electrophoresis, the above-described method may be used in conjunction with a wide variety of capillary electrophoresis systems. One such system is represented in FIG. 1. Further information concerning this sytem may be found in commonly owned U.S. Pat. No. 5,180,475 to Young et al.

Briefly, a capillary electrophoresis system 10 is shown as including a capillary tube 12 of fused silica having an inlet end 14 and an outlet end 16. The capillary tube has a zwitterionic coating as described above on its interior surface. The capillary tube is normally although not necessarily flexible. The capillary tube has an inside diameter which is in the range of about 25 μm to 75 μm, optimally about 50 μm, and an outside diameter that is typically although not necessarily in the range of 140 μm to 360 μm.

A component detecting means 18 is located along the length of the capillary tube 12. In capillary zone electrophoresis, ultraviolet absorbance detectors are commonly used, but other detectors are known. For example, detection may also be carried out using a chemiluminescence, refractive index, or conductivity detector. The optical coupling of the detector to the capillary tube permits detection of movement within the capillary tube.

The inlet end 14 of the capillary tube 12 is inserted into a container 20 having a sample vial 22. At the opposite side of the detector 18 is a buffer reservoir vial 24 that is in fluid communication with the outlet end 16 of the capillary tube. The buffer reservoir vial is housed within a container 26, and contains a standard buffer solution such as phosphate, borate, citrate, formate, succinate, acetate or the like, as well as optional additives, e.g., surfactants for altering selectivity or modifying EOF flow (e.g., anionic surfactants such as SDS, cationic surfactants such as DTAB, nonionic surfactants such as Triton X-100), hydrophilic polymers for decreasing EOF flow (e.g., polyvinyl alcohol), and the like. The pH of the buffer solution can be in the range of about 2 to 10, although for electronic control of EOF, the pH should be less than about 8 (note: with previously known systems, the pH had to be 4 or less for electronic control of EOF to be possible). The two containers 20 and 26 and the detector 18 rest on a table 28 or other suitable support.

A first high voltage power supply 30 is electrically connected to the supply vial 22 via a power line 32 that represents an anode electrode. The first power supply 30 provides a high voltage, shown in FIG. 1 as $-10$ kV, at the supply vial 22. However, this high voltage is not the potential difference across the capillary tube 12. Rather, the potential difference is determined by the voltage at the buffer reservoir vial 24. This voltage is provided by a second high voltage power supply 34 in electrical communication with the buffer reservoir vial 24 via a power line 36 that represents the cathode electrode. The second power supply 34 is illustrated as being set to provide a second high voltage of $-15$ kV. Thus, the potential difference across the length of the capillary tube 12 is 5 kV. A standard potential gradient in capillary zone electrophoresis is 200 V/cm. To achieve this, the length of the capillary tube would thus be 25 cm.

Each of the high voltage power supplies 30 and 34 is a bipolar device having a polarity-select switch 38 and 40 to adjust the polarity of the associated electrodes 32 and 36. Voltage-adjustment dials 42 and 44 allow a user to accurately set the outputs of the power supplies.

Figure 2:
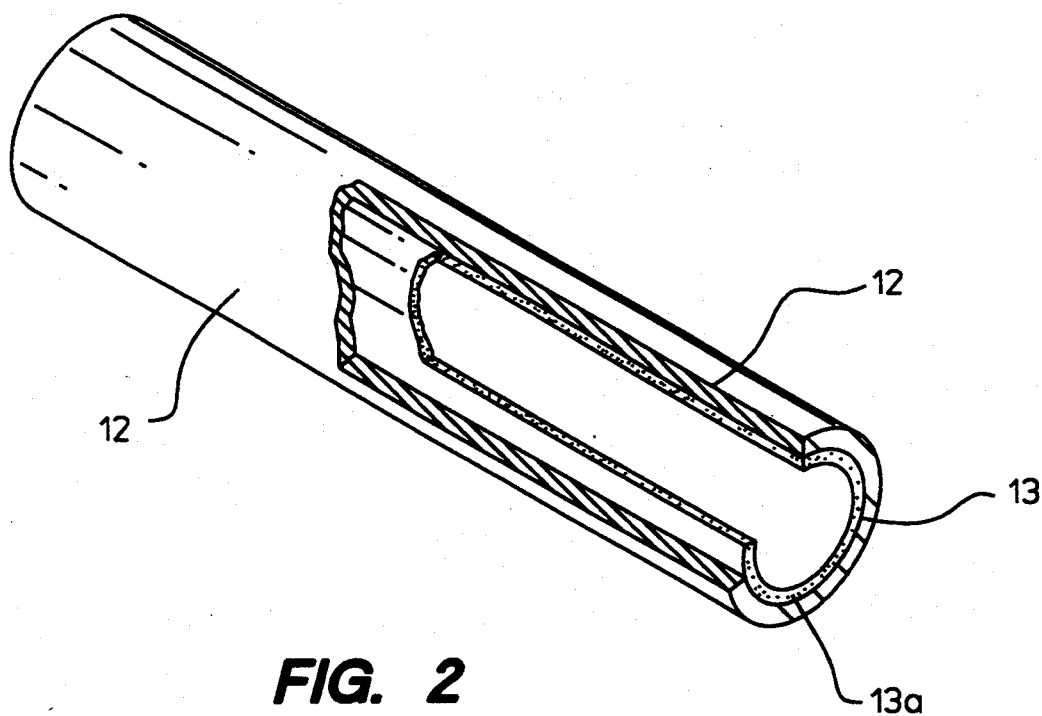
FIG. 2 is a perspective view of a coated capillary tube according to the invention.
Figure 3:
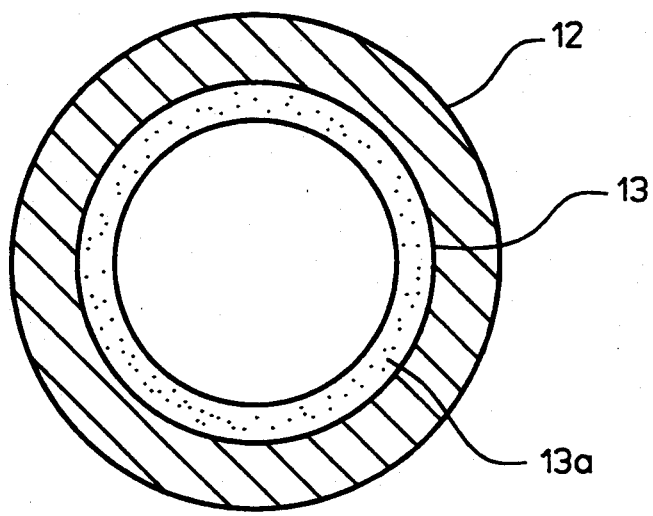
FIG. 3 is a cross-sectional view of a coated capillary tube according to the invention.

The coated capillary tube is shown in detail in FIGS. 2 and 3. As illustrated in those figures, the interior surface 13 of the tube 12 is provided with a zwitterionic coating 13a.

The aforementioned system, as noted, involves the use of two distinct high voltage power supplies. In alternative capillary electrophoresis systems, additional high voltage power supplies may be used, or the number may be reduced to one, provided that the exterior of the capillary tube is coated with a conductive or resistant coating (as described, for example, in U.S. Pat. No. 5,151,164 to Blanchard et al.).

In practice, the aforementioned technique and apparatus may be used to separate a wide variety of materials, including amino acids, chiral drugs, vitamins, pesticides, inorganic ions, organic acids, dyes, surfactants, peptides and proteins, carbohydrates, oligonucleotides and DNA restriction fragments, and even whole cells and virus particles. Separation is enhanced because the present methodology enables careful control of EOF velocity, even at higher pH's, and because the zwitterionic coating virtually eliminates ionic adsorption of molecular species on the capillary wall. Phosphoryl choline, in particular, has been found to be extremely useful in minimizing adsorption of protein molecules on the capillary surface.

While the present invention adapts most easily to use in capillary zone electrophoresis (also termed "free solution capillary electrophoresis"), it will be appreciated by those skilled in the art of electrophoretic separation that the invention may be used with other separation techniques as well, such as isotachophoresis, which separates sample constituents by mobilities, and to micellar electrokinetic capillary chromatography, a form of chromatography which uses a "stationary" phase that is subject to electroosmotic flow.

Experimental

The practice of the present invention will employ, unless otherwise indicated, conventional techniques of synthetic chemistry, silica surface modification, and the like, which are within the skill of the art. Such techniques are explained fully in the literature. See, e.g., Kirk-Othmer, Chemical Encyclopedia, Latest Edition, and *Silicon Compounds: Register and Review* (Petrarch Systems Silanes & Silicones), eds. R. Anderson et al. (1987).

It is to be understood that while the invention has been described in conjunction with the preferred specific embodiments thereof, that the description above as well as the examples which follow are intended to illustrate and not limit the scope of the invention. Other aspects, advantages and modifications within the scope of the invention will be apparent to those skilled in the art to which the invention pertains.

In the following examples, efforts have been made to insure accuracy with respect to numbers used (e.g., amounts, temperature, etc.) but some experimental error and deviation should be accounted for. Unless indicated otherwise, temperature is in degrees C and pressure is at or near atmospheric.

EXAMPLE 1

A polyimide coated silica capillary (50 μm i.d., obtained from Polymicro Technologies) is used for this experiment. Briefly, the interior of the capillary was coated with phosphoryl choline, as follows.

The capillary is flushed with 0.1M sodium hydroxide, or alternatively, with concentrated nitric acid, for a time period in the range of about 20 minutes to 24 hours, and then flushed with distilled and/or deionized water for 20 minutes to 1 hour. Using methods well-known to those skilled in the art of silica surface modification, the interior surface of the capillary is coated with the glycidoxypropyl moiety, e.g., using the reagent 3-glycidoxypropyldimethylethoxysilane (CAS 17963-04-1), which may be obtained from Hülz. Alternative reagents for carrying out this step include 3-glycido-xypropyltrimethoxysilane (CAS 2530-83-8) and 3-glycido-xypropylmethyldiethoxysilane (CAS 2897-60-1). The aforementioned reagent is dissolved in ethanol or toluene, the capillary filled with this solution, heated by immersion in an appropriate heating bath to 60° to 100° C. for 30 minutes to 1 hour, and then washed with distilled or deionized water. The capillary is then filled with a solution of phosphoryl chloride in pyridine, and subsequently treated with an aqueous pH 2 system. Further information concerning such a reaction may be found in Forrest and Todd, *J. Chem. Soc.* 3295 (1950), Baddiley and Thain, *J. Chem. Soc.* 903 (1953), and J. Riess, *Bull. Chim. Soc.* 18 (1965). The terminal phosphate is then ester-linked to choline by the action of an appropriate linking reagent, e.g., 1-(3-dimethylamino-propyl)-3-ethylcarbodiimide hydrochloride) (EDC; available from the Aldrich Chemical Company, Milwaukee Wis.) in water.

As an alternative to the glycidoxypropyldimethylethoxysilane route, aminopropyltrimethoxy silane may be used followed by ethylene chlorohydrin, such that the quaternary nitrogen atom is bonded through a propylene linkage to a silicon atom (in turn bound through an oxygen atom to a silicon atom in the silica surface), and a terminal hydroxyl group is provided. This latter functionality may then be reacted with excess $POCl_3$ in pyridine, as above, followed by acid hydrolysis, to provide a terminal phosphate group.

EXAMPLE 2

A zwitterionic species may also be bonded to the capillary wall through a direct silicon-carbon linkage. The linkage may be prepared as described by K. A. Cobb et al., in *Anal. Chem.* 62:2478–2483 (1990), cited earlier herein. Briefly, the inner surface of the capillary may be treated with $SOCl_2$, followed by reaction with a Grignard reagent such as propyl magnesium bromide. The terminus of the appended propyl group is then oxidized with a suitable oxidizing agent to provide a terminal hydroxyl group, followed by reaction with EDC, phosphoric acid, and $(CH_3)_3N^+$—$(CH_2)_2$— OH. The bonded zwitterionic species may be represented by the formula

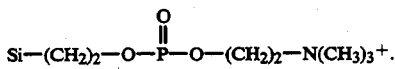

I claim:

1. A method for separating component elements contained within a sample solution using capillary electrophoresis, comprising:
   (a) providing an electrophoresis apparatus having a capillary tube, a means for introducing the sample solution into the capillary tube, a means for applying an electric field across the length of the capillary tube, and a component detecting means, wherein the capillary tube is comprised of fused silica having a zwitterionic coating on its interior surface, wherein the zwitterionic coating comprises a zwitterionic species covalently bound to the interior surface through a covalent linkage;
   (b) applying an electric field across the length of the capillary tube such that the sample solution moves through the tube and the component elements therein are spacially separated; and
   (c) detecting the presence of the individual component elements.

2. The method of claim 1, wherein the zwitterionic species is bound to the interior surface through a siloxane bond.

3. The method of claim 2, wherein the zwitterionic species is bound to the interior surface through an $Si^1$—O—$Si(OR^1)_2$—R linkage, wherein $Si^1$ is a silicon atom contained within the surface, R is a zwitterionic species, and $R^1$ is lower alkyl.

4. The method of claim 1, wherein the zwitterionic species is bound to the interior surface through a silicon-carbon bond.

5. The method of claim 1, wherein the zwitterionic species contains an $O^-$ moiety and a quaternary ammonium group.

6. The method of claim 5, wherein the zwitterionic species has the formula *—$L^1$—$X^-$—$L^2$—$NR_3^+$ in which $L^1$ and $L^2$ are optional linking groups, $X^-$ is an anionic species containing an $O^-$ moiety, R is lower alkyl, and * represents the point of attachment of the zwitterionic species to the interior surface.

7. The method of claim 5, wherein the zwitterionic species has the formula

*—$L^1$—$NR_2^+$—$X^-$ in which $L^1$ is an optional linking groups, $X^-$ is an anionic species containing an $O^-$ moiety, R is lower alkyl, and * represents the point of attachment of the zwitterionic species to the interior surface.

8. The method of claim 1, wherein the zwitterionic species is bound to the interior surface as $Si^1$—O—Si—$(CH_2)_n$—O—(CO)—$(CH_2)_n$—$OPO_2^-$—$(CH_2)_n$—$NR_3^+$ where $Si^1$ is a silicon atom contained within the surface, n is an integer in the range of 1 to 6 inclusive, and $R^3$ is lower alkyl.

9. A capillary for use in the electrophoretic separation of materials, comprising a tube of fused silica having an interior surface provided with a zwitterionic coating of a zwitterionic species bound to the interior surface through a covalent linkage.

10. An apparatus for conducting capillary electrophoresis to separate component elements contained in a sample solution, comprising:
    a supply vial for storing the sample solution;
    a buffer vial for storing buffer solution;
    a capillary tube that comprises a tube of fused silica with an interior provided with a zwitterionic coating comprising a zwitterionic species bound to the interior surface through a covalent linkage, and that has an inlet end through which sample solution is introduced from the supply vial;
    at least one high voltage power supply for applying an electric field across the capillary tube; and
    a detector positioned along the length of the capillary tube for sensing the presence of the separate component elements in the sample solution.

11. A method for separating component elements contained within a sample solution using capillary electrophoresis, comprising:
    (a) providing an electrophoresis apparatus having a capillary tube, a means for introducing the sample solution into the capillary tube, a means for applying an electric field across the length of the capillary tube, and a component detecting means, wherein the capillary tube is comprised of fused silica having a zwitterionic coating on its interior surface, wherein the zwitterionic coating comprises a zwitterionic species containing an $O^-$ moiety and a quaternary ammonium group, and wherein the zwitterionic species is ionically bound to the interior surface;

(b) applying an electric field across the length of the capillary tube such that the sample solution moves through the tube and the component elements therein are spacially separated; and (c) detecting the presence of the individual component elements.

12. A method for separating component elements contained within a sample solution using capillary electrophoresis, comprising:

(a) providing an electrophoresis apparatus having a capillary tube, a means for introducing the sample solution into the capillary tube, a means for applying an electric field across the length of the capillary tube, and a component detecting means, wherein the capillary tube is comprised of fused silica having a zwitterionic coating on its interior surface, wherein the zwitterionic coating comprises a zwitterionic species having the formula

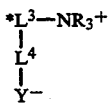

which $L^3$ is a linking group, $L^4$ is an optional linking group, $Y^-$ is an anionic species containing an $O^-$, R is lower alkyl, and * represents the point of attachment of the zwitterionic species to the interior surface, and wherein the zwitterionic species is bound to the interior surface through a covalent linkage, by adsorption or by ionic binding;

(b) applying an electric field across the length of the capillary tube such that the sample solution moves through the tube and the component elements therein are spacially separated; and (c) detecting the presence of the individual component elements.

13. A method for separating component elements contained within a sample solution using capillary electrophoresis, comprising:

(a) providing an electrophoresis apparatus having a capillary tube, a means for introducing the sample solution into the capillary tube, a means for applying an electric field across the length of the capillary tube, and a component detecting means, wherein the capillary tube is comprised of fused silica having a zwitterionic coating on its interior surface, wherein the zwitterionic coating comprises phosphoryl choline, and wherein the phosphoryl choline is bound to the interior surface through a covalent linkage, by adsorption or by ionic binding;

(b) applying an electric field across the length of the capillary tube such that the sample solution moves through the tube and the component elements therein are spacially separated; and (c) detecting the presence of the individual component elements.

14. A capillary for use in the electrophoretic separation of materials, comprising a tube of fused silica having an interior surface provided with a zwitterionic coating comprising phosphoryl choline, and wherein the phosphoryl choline is bound to the interior surface through a covalent linkage, by adsorption or by ionic binding.

* * * * *